(12) United States Patent
Tian et al.

(10) Patent No.: US 11,243,166 B2
(45) Date of Patent: Feb. 8, 2022

(54) INTRAOPERATIVE NEAR-INFRARED-I AND NEAR-INFRARED-II MULTI-SPECTRAL FLUORESCENT NAVIGATION SYSTEM AND METHOD OF USING THE SAME

(71) Applicant: INSTITUTE OF AUTOMATION, CHINESE ACADEMY OF SCIENCES, Beijing (CN)

(72) Inventors: Jie Tian, Beijing (CN); Zhenhua Hu, Beijing (CN); Caiguang Cao, Beijing (CN); Zeyu Zhang, Beijing (CN); Meishan Cai, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 428 days.

(21) Appl. No.: 16/545,023

(22) Filed: Aug. 20, 2019

(65) Prior Publication Data

US 2020/0132599 A1    Apr. 30, 2020

(30) Foreign Application Priority Data

Oct. 30, 2018  (CN) .......................... 201811277429.X (51) Int. Cl.
*G01N 21/47* (2006.01)
*A61B 6/00* (2006.01)
(Continued)

(52) U.S. Cl.
CPC ......... *G01N 21/4795* (2013.01); *A61B 6/482* (2013.01); *G01N 21/6456* (2013.01); *H04N 5/33* (2013.01)

(58) Field of Classification Search
CPC ............ G01N 21/4795; G01N 21/6456; A61B 6/482; A61B 34/20; A61B 2034/2065;
(Continued)

(56) References Cited

U.S. PATENT DOCUMENTS 11,002,680 B2 * 5/2021 Rizo .................... A61B 5/0071

FOREIGN PATENT DOCUMENTS

CN        105662354 A    6/2016
CN        108186115 A    6/2018
(Continued)

*Primary Examiner* — David P Porta
*Assistant Examiner* — Meenakshi S Sahu
(74) *Attorney, Agent, or Firm* — Kacvinsky Daisak Bluni PLLC (57) ABSTRACT

An intraoperative near-infrared-I and near-infrared-II multi-spectral fluorescent navigation system and method of using same includes a light source module for emitting white light and excitation light for illuminating tissue to be tested to generate an emission light. An optical information collection module includes a white light camera for collecting the white light image, and near infrared-I and near infrared-II fluorescence cameras for collecting the near infrared-I and near infrared-II fluorescence images. A central control module is coupled to the light source and the optical information collection modules. An image processing unit pre-processes the white light image, and the near infrared-I and near infrared-II fluorescence images, for de-noising and enhancement. The image processing unit performs a pseudo-color mapping on the images to obtain pseudo-color superimposed images of the near infrared-I and near infrared-II for a surgical region, and completes imaging of the intraoperative near-infrared-I and near-infrared-II multi-spectral fluorescent navigation system.

10 Claims, 3 Drawing Sheets

(51) Int. Cl.
*G01N 21/64* (2006.01)
*H04N 5/33* (2006.01)

(58) Field of Classification Search
CPC .... A61B 2090/3614; A61B 2090/3616; A61B 2090/376; A61B 2090/3762; A61B 5/0036; A61B 5/0071; A61B 5/4887; A61B 90/361; A61B 90/37; H04N 5/33; H04N 5/332
See application file for complete search history.

(56) References Cited

FOREIGN PATENT DOCUMENTS

| | | |
|---|---|---|
| CN | 108209878 A | 6/2018 |
| CN | 108309247 A | 7/2018 |
| CN | 108414442 A | 8/2018 |

* cited by examiner

INTRAOPERATIVE NEAR-INFRARED-I AND NEAR-INFRARED-II MULTI-SPECTRAL FLUORESCENT NAVIGATION SYSTEM AND METHOD OF USING THE SAME

CROSS-REFERENCE TO RELATED APPLICATION(S)

This application claims priority to pending Chinese Patent Application No. 201811277429.X filed on Oct. 30, 2018, the entire contents of which application is hereby incorporated by reference.

TECHNICAL FIELD

The present disclosure relates to the field of optical molecular imaging, and more particularly to an intraoperative near-infrared-I and near-infrared-II multi-spectral fluorescent navigation system and a method of using the same.

BACKGROUND

Intraoperative tumor microscopic lesions are difficult to be comprehensively detected, which is an important cause of cancer recurrence. So far, the most commonly used methods for detecting residual intraoperative cancer lesions in surgeons are: visual inspection, hand touch, rapid frozen section pathological detection, and intraoperative ultrasound. However, traditional detection techniques, as well as preoperative CT and MRI techniques, are still difficult to meet clinical requirements for comprehensive detection of intraoperative tumor microscopic lesions. Therefore, optimization of existing technologies and exploration of new imaging technologies have become hotspots in the field of imaging.

With the development of medical imaging technology, optical molecular imaging has become a new imaging technology which is widely used in basic research and clinical diagnosis of life sciences. The technology of optical molecular imaging spans many disciplines such as medicine, molecular biology, and computer science, and has advantages such as a high specificity, a high sensitivity, and a real-time dynamic imaging. Various analyses show that Indocyanine green (ICG)-mediated near-infrared fluorescence imaging technology can assist surgeons in real-time detection of a part of microscopic tumor lesions that are not found or missed by intraoperative ultrasound in cancer resection. Near-infrared fluorescence imaging is a technique for imaging lesions using near-infrared fluorescence, and may be divided into the near infrared-I fluorescence imaging operated under a wavelength from 700 nm to 900 nm and the near infrared-II fluorescence imaging operated under a wavelength from 1100 nm to 1700 nm. The near infrared-I imaging has the characteristics of low background noise and high signal intensity. The near infrared-II imaging has the advantages of a small scattering and absorption in biological tissues, a deep penetration depth, a weak auto-fluorescence of tissues, and a high signal-to-background ratio. The use of near-infrared signals for fluorescence imaging to detect tumor lesions is expected to improve the postoperative survival rate and quality of life of patients after having a tumor surgery; however, the existing near-infrared fluorescence imaging system has the disadvantages of a shallow imaging depth, a small signal-to-background ratio, and an inconspicuous tumor boundary.

SUMMARY (1) Technical Problems to be Solved

In view of the above problems, the present disclosure provides an intraoperative near-infrared-I and near-infrared-II multi-spectral fluorescent navigation system and a method of using the same, to alleviate the technical problems of the existing near-infrared fluorescence imaging system, such as a shallow imaging depth, a small signal-to-background ratio, and an inconspicuous tumor boundary.

(2) Technical Solution

In an aspect of the present disclosure, there is provided an intraoperative near-infrared-I and near-infrared-II multi-spectral fluorescent navigation system comprising: a light source module, configured to emit a white light and an excitation light, the white light and the excitation light illuminating a tissue to be tested, so as to generate an emission light; an optical information collection module, configured to collect a white light image, a near infrared-I image, and a near infrared-II image by using the emission light; and a central control module, coupled to the light source module and the optical information collection module respectively, and configured to control the light source module and the optical information collection module.

In the embodiment of the present disclosure, the light source module comprises: a white light emission device, configured to emit the white light; a laser, configured to emit the excitation light with a tunable wavelength; a fiber, configured to transmit the excitation light; and an adaption device, configured to couple the laser with the fiber.

In the embodiment of the present disclosure, the light source module further comprises:

a beam expander disposed at an end of the fiber, so as to diverge the excitation light transmitted from the fiber to a laser beam.

In the embodiment of the present disclosure, the light source module further comprises:

a protective glass, wherein a beam expander is disposed between the fiber and the protective glass, so as to transmit the beam-expanded excitation light to the protective glass, and the protective glass is configured to limit the excitation light.

In the embodiment of the present disclosure, the optical information collection module comprises: a white light camera, configured to collect the white light image; a near infrared-I fluorescence camera, configured to collect the near infrared-I fluorescence image; a near infrared-II fluorescence camera, configured to collect the near infrared-II fluorescence image; and zoom lenses mounted on the white light camera, the near infrared-I fluorescence camera, and the near infrared-II fluorescence camera through respective adaption rings, and configured to adjust the size of respective imaging area.

In the embodiment of the present disclosure, the optical information collection module further comprises:

a first data line, configured to transmit data of the white light camera; a second data line, configured to transmit data of the near infrared-I fluorescence camera; a third data line, configured to transmit data of the near infrared-II fluorescence camera; and a power line, configured to supply power to the white light camera, the near infrared-I fluorescence camera, and the near infrared-II fluorescence camera.

In the embodiment of the present disclosure, the optical information collection module further comprises: a first filter disposed between the near infrared-I fluorescence camera and a corresponding zoom lens, and configured to filter out optical signals outside the near infrared-I; and a second filter, disposed between the near infrared-II fluorescence camera and a corresponding zoom lens, and configured to filter out optical signals outside the near infrared-II band.

In the embodiment of the present disclosure, the central control module comprises: a signal control unit configured to control the light source module and the optical information collection module; a data reading unit configured to read data of the white light image, the near infrared-I fluorescence image, and the near infrared-II fluorescence image collected by the optical information collection module; and an image processing unit configured to preprocess the white light image, the near infrared-I fluorescence image, and the near infrared-II fluorescence image, so as to obtain a pseudo-color superimposed image of the near infrared-I and a pseudo-color superimposed image of the near infrared-II with respect to a surgical region; wherein the signal control unit, the data reading unit, and the image processing unit are communicatively coupled.

In the embodiment of the present disclosure, the central control module further comprises: an image display unit, configured to display the white light image, the near infrared-I fluorescence image, the near infrared-II fluorescence image, the pseudo-color superimposed image of the near infrared-I and the pseudo-color superimposed image of the near infrared-II, wherein the image display unit is communicably coupled to the signal control unit, the data reading unit, and the image processing unit.

In another aspect of the present disclosure, there is also provided a method of using the above intraoperative near-infrared-I and near-infrared-II multi-spectral fluorescent navigation system, the method comprising: step A: turning on the white light emission device, and outputting a control signal to the white light camera by the signal control unit of the central control module, so as to enable collecting the white light image by the white light camera; step B: turning off the white light emission device, turning on the laser to output the excitation light, and outputting a control signal to the near infra-red-I fluorescence camera and the near infra-red-II fluorescence camera by the signal control unit of the central control module, so as to enable collecting the near infrared-I fluorescence image and the near infrared-II fluorescence image, respectively; step C: preprocessing, by the image processing unit of the central control module, the white light image, the near infrared-I fluorescence image and the near infrared-II fluorescence image collected in the step A and the step B for de-noising and enhancement; step D: performing, by the image processing unit of the central control module, a pseudo-color mapping on images after being preprocessed in the step C, so as to obtain a pseudo-color superimposed image of the near infrared-I and a pseudo-color superimposed image of the near infrared-II for a surgical region, and completing the imaging of the intraoperative near-infrared-I and near-infrared-II multi-spectral fluorescent navigation system.

(3) Beneficial Effects

It can be seen from the above technical solutions that the intraoperative near-infrared-I and near-infrared-II multi-spectral fluorescent navigation system of the present disclosure and the method of using the same have at least one or a part of following beneficial effects:

(1) a small absorption and scattering in biological tissues;

(2) a weak auto-fluorescence of tissues and a high signal-to-background ratio;

(3) a stronger penetrating ability and a deeper imaging depth;

(4) a more realistic distribution of light signals, and a more accurate determination on tumor boundaries.

DETAILED DESCRIPTION

The present disclosure provides an intraoperative near-infrared-I and near-infrared-II multi-spectral fluorescent navigation system and a method of using the same. Compared with the conventional detection technology and the existing near infrared-I imaging technology, the present system additionally provides a near infrared-II imaging technology, which has a small absorption and scattering in biological tissues, and thus has the advantages of a deep penetration, a weak auto-fluorescence of tissues, and a high signal-to-background ratio.

To make the objectives, technical solutions, and advantages of the present disclosure clearer, the present disclosure will be further described in detail below in conjunction with the specific embodiments and with reference to the accompanying drawings.

Figure 1:
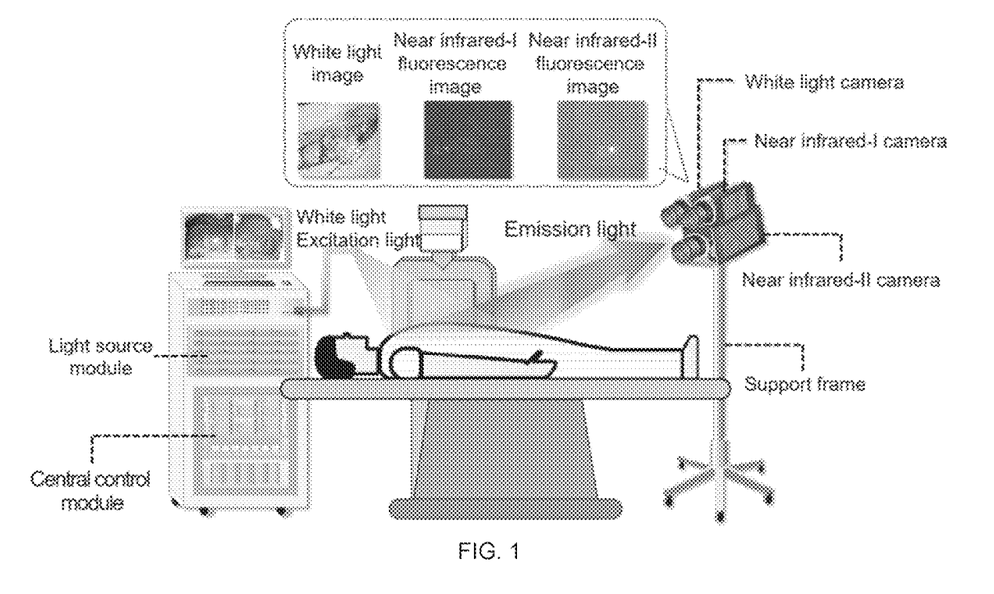
FIG. 1 is a schematic structural diagram of the intraoperative near-infrared-I and near-infrared-II multi-spectral fluorescent navigation system according to an embodiment of the present disclosure.
Figure 2:
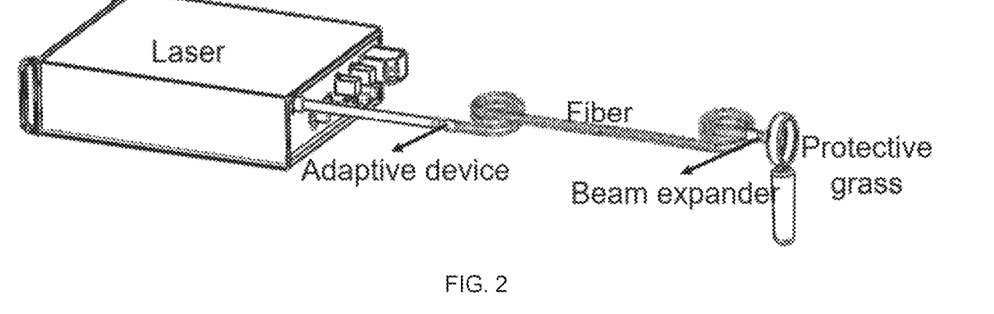
FIG. 2 is a schematic structural diagram of the light source module of the intraoperative near-infrared-I and near-infrared-II multi-spectral fluorescent navigation system according to an embodiment of the present disclosure.
Figure 3:
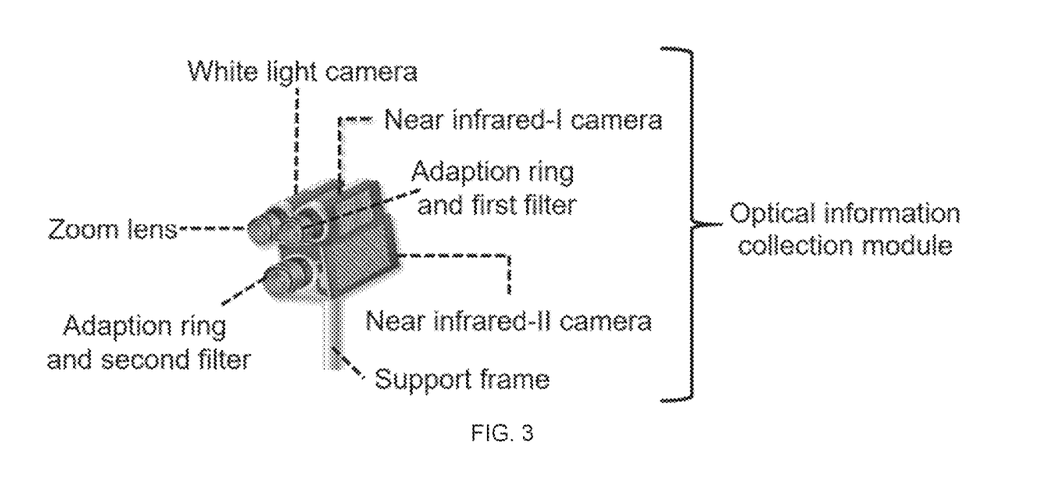
FIG. 3 is a schematic structural diagram of the optical information collection module of the intraoperative near-infrared-I and near-infrared-II multi-spectral fluorescent navigation system according to an embodiment of the present disclosure.

In the embodiment of the present disclosure, an intraoperative near-infrared-I and near-infrared-II multi-spectral fluorescent navigation system is provided. FIG. 1 is the schematic structural diagram of intraoperative near-infrared-I and near-infrared-II multi-spectral fluorescent navigation system, FIG. 2 is the schematic structural diagram of the light source module of the intraoperative near-infrared-I and near-infrared-II multi-spectral fluorescent navigation system, and FIG. 3 is the schematic structural diagram of the optical information collection module of the intraoperative near-infrared-I and near-infrared-II multi-spectral fluorescent navigation system. As shown in FIG. 1 to FIG. 3, the intraoperative near-infrared-I and near-infrared-II multi-spectral fluorescent navigation system includes:

a light source module, configured to emit a white light and an excitation light;

an optical information collection module, configured to obtain a white light image, a near infrared-I image, and a near infrared-II image; and a central control module, configured to: control the light source module and the optical information collection module; read the white light image, the near infrared-I fluorescence image, and the near infrared-II fluorescence image; and obtain the pseudo-color superimposed image of the near infrared-I and the pseudo-color superimposed image of the near infrared-II for the surgical region according to the white light image, the near infrared-I fluorescence image, and the near infrared-II fluorescence image.

The light source module illuminates the sample to obtain the white light image, the near infrared-I fluorescence image, and the near infrared-II fluorescence image.

According to a preferred embodiment, the intraoperative near-infrared-I and near-infrared-II multi-spectral fluorescent navigation system further includes an external packaging module. The external packaging module includes:

a support frame configured to support the optical information collection module of the intraoperative near-infrared-I and near-infrared-II multi-spectral fluorescent navigation system; wherein the support frame is used for ensuring balance and stability of the optical information collection module; and a connector disposed on the support frame for fixedly coupling the support frame and the optical information collection module.

According to a preferred embodiment, the intraoperative near-infrared-I and near-infrared-II multi-spectral fluorescent navigation system further includes:

an operating table configured to support a surgical patient or an object to be imaged, for lifting and/or translating the surgical patient or the object.

In the embodiment of the present disclosure, as shown in FIG. 1 to FIG. 3, the light source module includes:

a white light emission device, configured to emit the white light;

a laser, configured to emit the excitation light with a tunable wavelength;

a fiber, configured to transmit the excitation light to a imaging area; wherein the fiber is made of glass, and the length of the fiber may be, for example, 3 meters; and an adaption device, configured to couple the laser with the fiber.

According to a preferred embodiment, the light source module further includes:

a beam expander disposed at an end of the fiber, so as to diverge the excitation light transmitted from the fiber to a larger laser beam.

According to a preferred embodiment, the light source module further includes:

a protective glass, wherein a beam expander is disposed between the fiber and the protective glass, so as to transmit the beam-expanded excitation light to the protective glass, and the protective glass is configured to limit the excitation light diverged by the beam expander to a small range to protect other sub-components.

In the embodiment of the present disclosure, the optical information collection module is used for collecting the white light, the near infrared-I fluorescence and the near infrared-II fluorescence lights. As shown in FIG. 1 to FIG. 3, the optical information collection module includes:

a white light camera, configured to collect the white light image;

a near infrared-I fluorescence camera, configured to collect the near infrared-I fluorescence image;

a near infrared-II fluorescence camera, configured to collect the near infrared-II fluorescence image;

zoom lenses configured to adjust the size of the imaging area; and adaption rings configured to couple the camera with the respective zoom lens.

According to a preferred embodiment, the optical information collection module further includes:

a first data line, configured to transmit data of the white light camera;

a second data line, configured to transmit data of the near infrared-I fluorescence camera;

a third data line, configured to transmit data of the near infrared-II fluorescence camera; and a power line, configured to supply power to the white light camera, the near infrared-I fluorescence camera, and the near infrared-II fluorescence camera.

The white light camera and the near infrared-I fluorescence camera may be implemented by pco.edge 5.5 cameras with a high-speed, a high-sensitivity and a high-resolution, and the near infrared-II fluorescence camera may be implemented by PI NIRvana 640 camera with an operating temperature of minus 80 degrees Celsius.

The first data line may couple the white light camera to the central control module through a USB3.0 interface; the second data line may couple the near infrared-I fluorescence camera to the central control module through the USB3.0 interface; and the third data line may couple the near infrared-II fluorescence camera to the central control module through the RJ45 interface.

The power line includes a first power line, a second power line, and a third power line, and each power line couples the respective camera to a 220V voltage through a power adapter.

According to a preferred embodiment, the optical information collection module further includes:

a first filter disposed between the near infrared-I fluorescence camera and a corresponding zoom lens;

wherein the first filter may be a band-pass filter for near infrared-I signal, and disposed on the adaption ring to filter out optical signals outside the near infrared-I;

a second filter, disposed between the near infrared-II fluorescence camera and a corresponding zoom lens;

wherein the second filter may be a near infrared-II signal band-pass filter, and disposed on the adaption ring to filter out optical signals outside the near infrared-II.

In the embodiment of the present disclosure, the central control module includes:

a signal control unit configured to control the light source module and the optical information collection module;

a data reading unit configured to read data of the white light image, the near infrared-I fluorescence image, and the near infrared-II fluorescence image collected by the optical information collection module; and an image processing unit configured to preprocess the white light image, the near infrared-I fluorescence image, and the near infrared-II fluorescence image, so as to obtain a pseudo-color superimposed image of the near infrared-I and a pseudo-color superimposed image of the near infrared-II with respect to a surgical region.

The signal control unit, the data reading unit, and the image processing unit are communicatively coupled.

The signal control unit may be used, for example, to output control signals for the light source module and the optical information collection module from a computer; the data reading unit may be used, for example, to read the signals collected by the optical information collection module by a computer; and the image processing unit may be used, for example, to perform processing such as correcting, de-noising, pseudo-color superimposing, and the like on the collected optical information.

According to a preferred embodiment, the central control module further includes:

an image display unit, configured to display the white light image, the near infrared-I fluorescence image, the near infrared-II fluorescence image, the pseudo-color superimposed image of the near infrared-I and the pseudo-color superimposed image of the near infrared-II. The image display unit is communicably coupled to the signal control unit, the data reading unit, and the image processing unit.

In the embodiment of the present disclosure, the signal control unit outputs control signals, so as to control the collection cameras and set the sequence for collection and related parameters. The data reading unit reads, through the data line of each camera, the white light image, the near infrared-I fluorescence image, and the near infrared-II fluorescence image that have been collected. Then, the collected information is processed by the image processing unit, and image processing such as de-noising and enhancement is performed on the white light image and the fluorescence images. According to the preliminary processed white light image and fluorescence images, the registration parameters are calculated. Then, the fluorescence images are pseudo-color mapped, in particular, the pseudo-colors are superimposed on the white light image respectively to obtain the pseudo-color superimposed image of the near infrared-I and the pseudo-color superimposed image of the near infrared-II. Finally, the image display unit displays the white light image, the pseudo-color superimposed image of the near infrared-I and the pseudo-color superimposed image of the near infrared-II.

Figure 4:
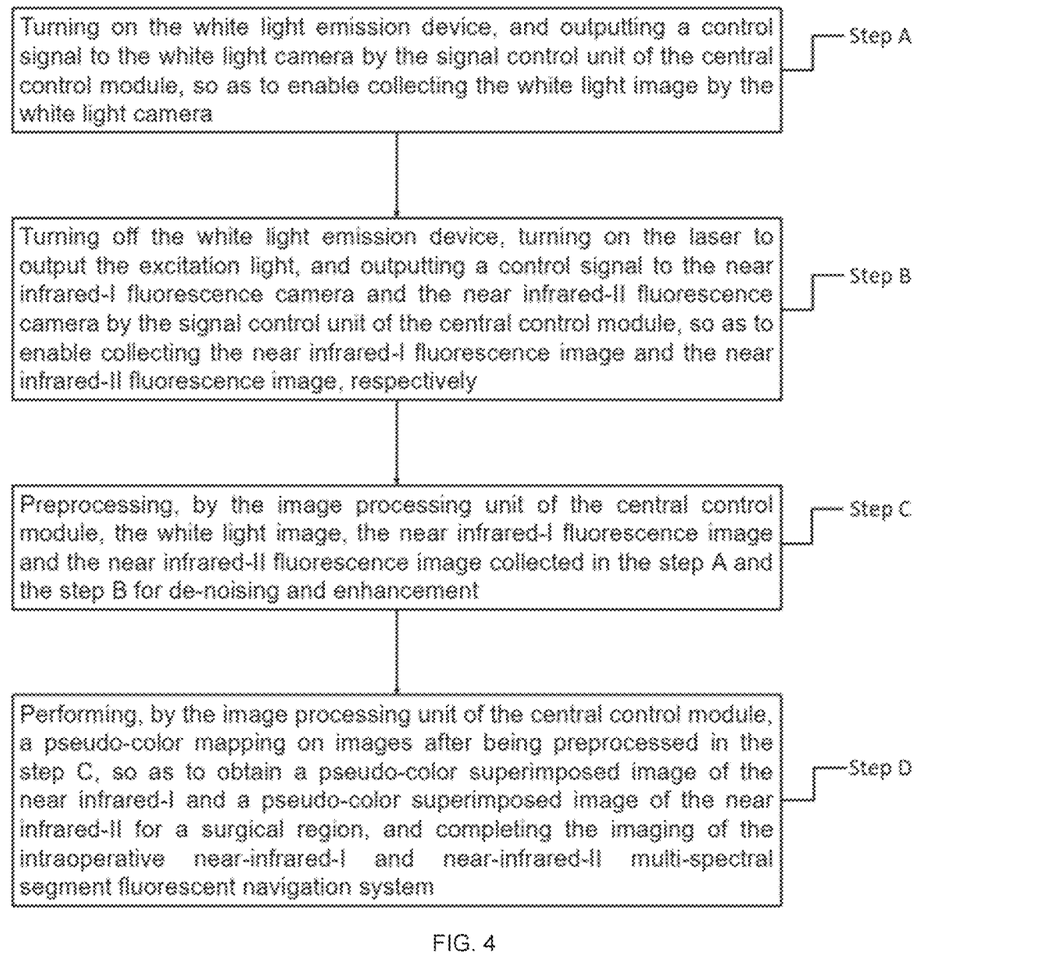
FIG. 4 is a flow chart showing the method of using the intraoperative near-infrared-I and near-infrared-II multi-spectral fluorescent navigation system according to an embodiment of the present disclosure.

As described above, in the embodiment of the present disclosure, there is also provided a method of using the intraoperative near-infrared-I and near-infrared-II multi-spectral fluorescent navigation system, which is based on the above-described intraoperative near-infrared-I and near-infrared-II multi-spectral fluorescent navigation system for imaging. The intraoperative near-infrared-I and near-infrared-II multi-spectral fluorescent navigation system is assembled and the support frame is adjusted so that the imaging area is as close as possible to the center of the view field. FIG. 4 is the schematic flow chart showing the method of using the intraoperative near-infrared-I and near-infrared-II multi-spectral fluorescent navigation system. As shown in FIG. 4, the method includes:

step A: turning on the white light emission device, and outputting a control signal to the white light camera by the signal control unit of the central control module, so as to enable collecting the white light image by the white light camera;

step B: turning off the white light emission device, turning on the laser to output the excitation light, and outputting a control signal to the near infrared-I fluorescence camera and the near infrared-II fluorescence camera by the signal control unit of the central control module, so as to enable collecting the near infrared-I fluorescence image and the near infrared-II fluorescence image, respectively;

step C: preprocessing, by the image processing unit of the central control module, the white light image, the near infrared-I fluorescence image and the near infrared-II fluorescence image collected in the step A and the step B for de-noising and enhancement and the like;

step D: performing, by the image processing unit of the central control module, a pseudo-color mapping on images after being preprocessed in the step C, so as to obtain a pseudo-color superimposed image of the near infrared-I and a pseudo-color superimposed image of the near infrared-II for a surgical region, and completing the imaging of the intraoperative near-infrared-I and near-infrared-II multi-spectral fluorescent navigation system.

The present disclosure relates to the near-infrared fluorescence surgical navigation technology, and realize near-infrared fluorescence imaging of tumor microscopic lesions in patients by combining white light image with near-infrared fluorescence image and using image processing algorithm to process those images. In addition, the present disclosure further constructs an intraoperative near-infrared-I and near-infrared-II multi-spectral fluorescent navigation system which can realize the detection of microscopic tumors in patients.

Heretofore, the embodiments of the present disclosure have been described in detail in conjunction with the accompanying drawings. It should be noted that the implementations that are not shown or described in the drawings or the text of the specification are all known to those of ordinary skill in the art and are not described in detail. In addition, the above definitions of the various elements and methods are not limited to the specific structures, shapes or manners mentioned in the embodiments, and those skilled in the art may simply modify or replace them.

In light of the above description, those skilled in the art should have a clear understanding of the intraoperative near-infrared-I and near-infrared-II multi-spectral fluorescent navigation system according to the present disclosure.

In summary, the present disclosure provides an intraoperative near-infrared-I and near-infrared-II multi-spectral fluorescent navigation system and a method of using the same. Compared with the conventional detection technology and the existing near infrared-I imaging technology, the system additionally provides a near infrared-II imaging technique, which has a weak absorption and scattering in biological tissues, and thus has the advantages of a deep penetration, a weak auto-fluorescence of tissues, and a high signal-to-background ratio.

It should also be noted that the directional terms mentioned in the embodiments, such as "upper", "lower", "front", "back", "left", "right", and the like, are only referring to the directions of the drawings, and not used to limit the scope of protection of the present disclosure. The same elements are denoted by the same or similar reference numerals throughout the drawings. Conventional structures or configurations will be omitted when they may cause confusion to the understanding of the present disclosure.

The shapes and sizes of the various components in the drawings do not reflect the true size and proportions, but merely illustrate the contents of the embodiments of the present disclosure. In addition, in the claims, any reference signs placed between parentheses shall not be construed as a limitation.

Unless otherwise stated, numerical parameters in the present specification and the appended claims are approximations, and can vary depending upon the desired characteristics obtained by the teachings of the disclosure. In particular, all numbers expressing the composition contents, reaction conditions, and the like, which are used in the specification and claims, are to be understood as being modified by the term "about" in all cases. In general, it is meant to include a variation of ±10% for a specific amount in some embodiments, ±5% in some embodiments, ±1% in some embodiments and ±0.5% in some embodiments.

The word "comprising" does not exclude the presence of the elements or steps that are not recited in the claims. The word "a", "an" or "one" before the element does not exclude the presence of a plurality of such elements.

The ordinal numbers used in the specification and claims (such as "first", "second", "third" and the like) are used to modify the corresponding elements, and do not mean that the elements have any ordinal numbers. They do not represent the order of one element and another element, or the order of the method of manufacture. They are only used to clearly distinguish one element with a certain name from another element with the same name.

In addition, unless specifically stated or steps that must occur in sequence, the order of the above steps is not limited to the above, and may be varied or rearranged depending on the desired design. The above embodiments may be used in combination with each other or in combination with other embodiments based on design and reliability considerations, that is, the technical features in different embodiments may be freely combined to form more embodiments.

Those skilled in the art will appreciate that the modules in the devices of the embodiments may be adaptively changed and placed in one or more devices different from the embodiment. The modules or units or components of the embodiments may be combined into one module or unit or component, and they may be divided into a plurality of sub-modules or sub-units or sub-components. All features disclosed in the specification, including the accompanying claims, the abstract and the drawings, and all processes or units of any methods or devices so disclosed, may be combined by any combination, unless at least some of such features and/or processes or units are mutually exclusive. Unless otherwise expressly stated, each feature disclosed in this specification, including the accompanying claims, the abstract and the drawings, may be replaced by alternative features that provide the same, equivalent or similar purpose. In the unit claims enumerating several means, several of these means may be embodied by the same hardware item.

Similarly, it is understood that, in order to simplify the present disclosure and to help understand one or more of the various aspects, in the above description of the exemplary embodiments of the present disclosure, the various features of the present disclosure are sometimes grouped together into a single embodiment, figure, or the description thereof. However, the method disclosed is not to be interpreted as reflecting the intention that the claimed invention requires more features than those specifically recited in each claim. Rather, as reflected in the following claims, the disclosed aspects are less than all features of the single embodiments disclosed above. Therefore, the claims following the specific embodiments are hereby explicitly incorporated into the specific embodiments, and each of the claims is to be a separate embodiment of the present disclosure.

The specific embodiments described above further illustrate the purpose, technical solutions and beneficial effects of the present disclosure. It should be understood that the above description is only specific embodiments of the present disclosure and is not used to limit the present disclosure. Any modification, equivalent replacement, and improvement made within the spirit and principle of the present disclosure shall fall within the protection scope of the present disclosure.

We claim:

1. An intraoperative near-infrared-I and near-infrared-II multi-spectral fluorescent navigation system comprising:
   a light source module configured to emit a white light and an excitation light, the white light and the excitation light illuminating a tissue to be tested, so as to generate an emission light;
   an optical information collection module configured to collect a white light image, a near infrared-I image, and a near infrared-II image using the emission light; and
   a central control module coupled to the light source module and the optical information collection module respectively, and configured to control the light source module and the optical information collection module.

2. The intraoperative near-infrared-I and near-infrared-II multi-spectral fluorescent navigation system of claim 1, wherein the light source module comprises:
   a white light emission device configured to emit the white light;
   a laser configured to emit the excitation light with a tunable wavelength;
   a fiber configured to transmit the excitation light; and
   an adaption device configured to couple the laser with the fiber.

3. The intraoperative near-infrared-I and near-infrared-II multi-spectral fluorescent navigation system of claim 2, wherein the light source module further comprises:
   a beam expander disposed at an end of the fiber so as to diverge the excitation light transmitted from the fiber to a laser beam.

4. The intraoperative near-infrared-I and near-infrared-II multi-spectral fluorescent navigation system of claim 2, wherein the light source module further comprises:
   a protective glass, wherein a beam expander is disposed between the fiber and the protective glass, so as to transmit the beam-expanded excitation light to the protective glass, and the protective glass is configured to limit the excitation light.

5. The intraoperative near-infrared-I and near-infrared-II multi-spectral fluorescent navigation system of claim 1, wherein the optical information collection module comprises:
   a white light camera configured to collect the white light image;
   a near infrared-I fluorescence camera configured to collect the near infrared-I fluorescence image;
   a near infrared-II fluorescence camera configured to collect the near infrared-II fluorescence image; and
   zoom lenses mounted on the white light camera, the near infrared-I fluorescence camera, and the near infrared-II fluorescence camera, through respective adaption rings, and configured to adjust the size of respective imaging area.

6. The intraoperative near-infrared-I and near-infrared-II multi-spectral fluorescent navigation system of claim 5, wherein the optical information collection module further comprises:
   a first data line configured to transmit data of the white light camera;
   a second data line configured to transmit data of the near infrared-I fluorescence camera;
   a third data line configured to transmit data of the near infrared-II fluorescence camera; and
   a power line configured to supply power to the white light camera, the near infrared-I fluorescence camera, and the near infrared-II fluorescence camera.

7. The intraoperative near-infrared-I and near-infrared-II multi-spectral fluorescent navigation system of claim 5, wherein the optical information collection module further comprises:

a first filter disposed between the near infrared-I fluorescence camera and a corresponding zoom lens, and configured to filter out optical signals outside the near infrared-I; and a second filter disposed between the near infrared-II fluorescence camera and a corresponding zoom lens, and configured to filter out optical signals outside the near infrared-II.

8. The intraoperative near-infrared-I and near-infrared-II multi-spectral fluorescent navigation system of claim 1, wherein the central control module comprises:

a signal control unit configured to control the light source module and the optical information collection module;

a data reading unit configured to read data of the white light image, the near infrared-I fluorescence image, and the near infrared-II fluorescence image collected by the optical information collection module; and an image processing unit configured to preprocess the white light image, the near infrared-I fluorescence image, and the near infrared-II fluorescence image, so as to obtain a pseudo-color superimposed image of the near infrared-I and a pseudo-color superimposed image of the near infrared-II with respect to a surgical region;

wherein the signal control unit, the data reading unit, and the image processing unit are communicatively coupled.

9. The intraoperative near-infrared-I and near-infrared-II multi-spectral fluorescent navigation system of claim 8, wherein the central control module further comprises:

an image display unit configured to display the white light image, the near infrared-I fluorescence image, the near infrared-II fluorescence image, the pseudo-color superimposed image of the near infrared-I, and the pseudo-color superimposed image of the near infrared-II, wherein the image display unit is communicably coupled to the signal control unit, the data reading unit, and the image processing unit.

10. A method of using the intraoperative near-infrared-I and near-infrared-II multi-spectral fluorescent navigation system of claim 1, the method comprising:

step A: turning on the white light emission device, and outputting a control signal to the white light camera by the signal control unit of the central control module, so as to enable collecting the white light image by the white light camera;

step B: turning off the white light emission device, turning on the laser to output the excitation light, and outputting a control signal to the near infrared-I fluorescence camera and the near infrared-II fluorescence camera by the signal control unit of the central control module, so as to enable collecting the near infrared-I fluorescence image and the near infrared-II fluorescence image, respectively;

step C: preprocessing, by the image processing unit of the central control module, the white light image, the near infrared-I fluorescence image and the near infrared-II fluorescence image collected in the step A and the step B for de-noising and enhancement;

step D: performing, by the image processing unit of the central control module, a pseudo-color mapping on images after being preprocessed in the step C, so as to obtain a pseudo-color superimposed image of the near infrared-I and a pseudo-color superimposed image of the near infrared-II for a surgical region, and completing the imaging of the intraoperative near-infrared-I and near-infrared-II multi-spectral fluorescent navigation system.

* * * * *